(12) United States Patent
Sakamaki et al.

(10) Patent No.: US 12,215,140 B2
(45) Date of Patent: Feb. 4, 2025

(54) METHOD OF STABILIZING PROTEIN CONTAINED IN SPECIMEN AND SOLUTION FOR STABILIZING PROTEIN CONTAINED IN SPECIMEN

(71) Applicant: EIKEN KAGAKU KABUSHIKI KAISHA, Tokyo (JP)

(72) Inventors: Nozomi Sakamaki, Tochigi (JP); Hidenori Taguchi, Tochigi (JP); Mitsuru Makinodan, Tochigi (JP); Miyu Yamada, Tochigi (JP)

(73) Assignee: EIKEN KAGAKU KABUSHIKI KAISHA, Tokyo (JP)

(*) Notice: Subject to any disclaimer, the term of this patent is extended or adjusted under 35 U.S.C. 154(b) by 1107 days.

(21) Appl. No.: 16/977,338

(22) PCT Filed: Feb. 28, 2019

(86) PCT No.: PCT/JP2019/007867
§ 371 (c)(1),
(2) Date: Sep. 1, 2020

(87) PCT Pub. No.: WO2019/168109
PCT Pub. Date: Sep. 6, 2019

(65) Prior Publication Data
US 2020/0407425 A1    Dec. 31, 2020

(30) Foreign Application Priority Data
Mar. 2, 2018  (JP) ................. 2018-037227

(51) Int. Cl.
*C07K 14/805* (2006.01)
*G01N 33/72* (2006.01)

(52) U.S. Cl.
CPC .......... *C07K 14/805* (2013.01); *G01N 33/72* (2013.01); *G01N 33/721* (2013.01)

(58) Field of Classification Search
CPC ..... C07K 14/805; G01N 33/72; G01N 33/721
See application file for complete search history.

(56) References Cited

U.S. PATENT DOCUMENTS

| | | | | |
|---|---|---|---|---|
| 4,861,772 A | * | 8/1989 | Merz | A61K 31/55 514/219 |
| 8,445,719 B2 | | 5/2013 | Sugo | |
| 2011/0174621 A1 | * | 7/2011 | Yonehara | G01N 27/44747 204/549 |
| 2019/0056328 A1 | * | 2/2019 | Olivo | G01N 21/658 |

FOREIGN PATENT DOCUMENTS

| | | |
|---|---|---|
| EP | 0997527 B1 | 6/2010 |
| EP | 2204648 B1 | 11/2016 |
| GB | 2353797 A | 3/2001 |
| JP | S63243756 A | 10/1988 |
| JP | 8262020 A2 | 10/1996 |
| JP | 9224942 A2 | 9/1997 |
| JP | H10132824 A | 5/1998 |
| JP | 2000206117 A | 7/2000 |
| JP | 2000258420 A | 9/2000 |
| JP | 2009097956 A | 5/2009 |
| JP | 2016191580 A | 11/2016 |
| WO | 2011058958 A1 | 5/2011 |

OTHER PUBLICATIONS

Search report in corresponding EP19761056.1 dated Jan. 31, 2022 (pp. 1-9).
International Search Report PCT/JP2019/007867 dated May 28, 2019 (pp. 1-4).
Frantzen et al., "Protein-boronic acid conjugates and their binding to low-molecularmass cis-diols and glycated hemoglobin", Journal of Chromatography B: Biomedical Sciences and Applications, 1995, 670(1), pp. 37-45.
Office Action in corresponding Taiwanese Application No. 108107034 dated Apr. 8, 2022 (pp. 1-3).
Office Action in corresponding CN 201980016412.5 dated Jul. 1, 2023 (pp. 1-9).

* cited by examiner

*Primary Examiner* — Changhwa J Cheu
(74) *Attorney, Agent, or Firm* — MILLEN, WHITE, ZELANO & BRANIGAN, P.C.; Ryan R. Pool

(57) ABSTRACT

The present invention provides a method of stabilizing a protein. The method includes a step of causing a protein contained in a specimen derived from a living body to coexist with an arylboronic acid. The protein contained in the specimen derived from the living body is at least one type selected from the group consisting of hemoglobin, haptoglobin, and a hemoglobin-haptoglobin complex. According to the present invention, it is possible to stabilize a protein such as a blood protein contained in the specimen derived from a living body. The present invention further provides a stabilizing solution for stabilizing a protein contained in a specimen derived from a living body and a method and a kit for detecting a protein contained in a specimen derived from a living body.

19 Claims, No Drawings

METHOD OF STABILIZING PROTEIN CONTAINED IN SPECIMEN AND SOLUTION FOR STABILIZING PROTEIN CONTAINED IN SPECIMEN

TECHNICAL FIELD

The present invention relates to a method for stabilizing a protein contained in a specimen derived from a living body, a solution for stabilizing a protein contained in a specimen derived from a living body, and a method and a kit for detecting a protein contained in a specimen derived from a living body.

BACKGROUND ART

Detection of proteins contained in specimens such as feces, urine, and saliva is useful for diagnosis of many diseases. For example, a fecal occult blood test of detecting blood in a fecal specimen enables acquisition of important information in the diagnosis of gastrointestinal diseases such as colon cancer. Known methods of detecting blood proteins or the like such as hemoglobin, haptoglobin, and a hemoglobin-haptoglobin complex contained in a specimen such as feces include an immunological measurement method for detection using an antibody which reacts with these proteins.

A specimen to be subjected for an occult blood test is usually collected by a subject in a container containing a preservation solution, and is sent to an inspection institution such as a hospital. In many cases, the preservation solution (sample) containing a specimen (the preservation solution containing a specimen will be referred to as a sample herein) is often exposed to unfavorable temperature conditions for preservation because its transportation requires several days and temperature management during the transportation is generally difficult. If proteins such as blood proteins contained in a specimen are denatured due to temperature conditions during the transportation and the like or decomposed or modified by bacteria or enzymes contained in the specimen to change the structure of the epitope or its vicinity, then the antibody cannot recognize the proteins contained in the feces, and accurate measurement by the immunological measurement method will be difficult. In particular, hemoglobin is unstable in the solution and liable to be denatured or decomposed under high temperature conditions.

As a technique for stabilizing hemoglobin in the preservation solution, for example, various methods have been proposed, including a method of adding an antibacterial agent such as thimerosal or chlorhexidine (e.g., Patent Document 1), a method of adding a protease inhibitor (e.g., Patent Document 2), a method of adding a glycosidase-type lytic enzyme (e.g., Patent Document 3), a method of adding an enzymatic decomposition product of hemoglobin (e.g., Patent Document 4), a method of adding an organic acid such as malic acid (e.g., Patent Document 5), a method of adding iminocarboxylic acid (e.g., Patent Document 6), and a method of adding haloalkanesulfonic acid (e.g., Patent Document 7).

Furthermore, there has been known a method of adding haptoglobin to stabilize hemoglobin (e.g., Patent Document 8). It is known that haptoglobin exists in blood of a wide variety of animals, rapidly binds to hemoglobin, and forms a stable hemoglobin-haptoglobin complex (Hb-Hp complex). By preliminarily adding haptoglobin to the preservation solution or the like which preserves a specimen such as feces, when the specimen such as feces is added to the preservation solution, the hemoglobin contained in the specimen derived from a living body can be made to a stable hemoglobin-haptoglobin complex.

However, because hemoglobin is extremely unstable, even such methods of stabilizing hemoglobin have not yet sufficiently prevented the denaturation or decomposition. In this context, a method of measuring transferrin which is more excellent in the stability than hemoglobin is also known as a method of detecting the fecal occult blood (e.g., Patent Document 9), but the transferrin exists in blood only at about 1/60 as compared with hemoglobin, and the problem is therefore that the sensitivity is low.

PRIOR ART DOCUMENTS

Patent Documents

[Patent Document 1] JP63-271160A
[Patent Document 2] JP3-279859A
[Patent Document 3] JP63-246667A
[Patent Document 4] JP11-218533A
[Patent Document 5] JP2003-14768A
[Patent Document 6] JP2009-097956A
[Patent Document 7] JP2016-191580A
[Patent Document 8] JP10-132824A
[Patent Document 9] JP63-246668A

SUMMARY OF THE INVENTION

Problems to be Solved by the Invention

A considerable number of bacteria and enzymes that cause decomposition and modification of proteins such as hemoglobin exist in a specimen derived from a living body, such as feces, urine, or saliva, and particularly in feces; therefore, even proteins having relatively high stability, such as a hemoglobin-haptoglobin complex, may be decomposed or modified.

An object of the present invention is therefore to provide a method of enhancing the stability of a protein contained in a specimen derived from a living body even under unfavorable temperature conditions in which decomposition, denaturation, and the like are likely to occur.

Means For Solving the Problems (1) A method of stabilizing a protein contained in a specimen derived from a living body, the method including a step of causing the protein contained in the specimen derived from the living body to coexist with an arylboronic acid, wherein
   the protein contained in the specimen derived from the living body is at least one type selected from the group consisting of hemoglobin, haptoglobin, and a hemoglobin-haptoglobin complex.
(2) The method according to (1), wherein the arylboronic acid is at least one type selected from the group consisting of phenylboronic acid and derivatives thereof.
(3) The method according to (1)(2), wherein the arylboronic acid is at least one type selected from the group consisting of phenylboronic acid, hydroxyphenylboronic acid, carboxyphenylboronic acid, aminophenylboronic acid, and salts thereof.
(4) The method according to (1) to (3), wherein
   the step is a step of dispersing the protein contained in the specimen derived from the living body in a solution containing the arylboronic acid, and the concentration of the arylboronic acid in the solution is 0.1 mmol/L or more.

(5) The method according to (1) to (4), wherein the step is a step of causing the protein contained in the specimen derived from the living body to coexist with the arylboronic acid and a sugar.

(6) The method according to (5), wherein the sugar is at least one type selected from the group consisting of sugar alcohol, monosaccharide, and disaccharide.

(7) The method according to (5)(6), wherein the sugar is at least one type selected from the group consisting of sorbitol, glucose, mannitol, fructose, xylitol, erythritol, sucrose, trehalose, lactose, and maltose.

(8) The method according to (5) to (7), wherein
the step is a step of dispersing the protein contained in the specimen derived from the living body in a solution containing the arylboronic acid and the sugar, and
the concentration of the sugar in the solution is 5 mmol/L or more.

(9) The method according to (1) to (8), wherein
the specimen derived from the living body contains at least hemoglobin, and
the method includes a step of bringing the hemoglobin and haptoglobin into contact with each other to form a complex of hemoglobin and haptoglobin.

(10) The method according to (1) to (9), wherein the specimen derived from the living body is feces, saliva, or urine.

(11) A stabilizing solution for stabilizing a protein contained in a specimen derived from a living body, wherein
the stabilizing solution contains an arylboronic acid, and
the protein contained in the specimen derived from the living body is at least one type selected from the group consisting of hemoglobin, haptoglobin, and a hemoglobin-haptoglobin complex.

(12) The stabilizing solution according to (11), wherein the arylboronic acid is at least one type selected from the group consisting of phenylboronic acid and derivatives thereof.

(13) The stabilizing solution according to (11)(12), wherein the arylboronic acid is at least one type selected from the group consisting of phenylboronic acid, hydroxyphenylboronic acid, carboxyphenylboronic acid, aminophenylboronic acid, and salts thereof.

(14) The stabilizing solution according to (11) to (13), containing a sugar.

(15) The stabilizing solution according to (14), wherein the sugar is at least one type selected from the group consisting of sorbitol, glucose, mannitol, fructose, xylitol, erythritol, sucrose, trehalose, lactose, and maltose.

(16) The stabilizing solution according to (11) to (15), containing haptoglobin.

(17) The stabilizing solution according to (11) to (16), wherein the specimen is feces, saliva, or urine.

(18) The stabilizing solution according to (11) to (17), wherein the stabilizing solution is a solution for preserving the specimen derived from the living body.

(19) A method of detecting a protein in a specimen derived from a living body, the method comprising:
a step of adding the specimen derived from the living body to the stabilizing solution according to (11) to (18) to obtain a sample containing the specimen; and
a step of detecting the protein in the sample by an immunological measurement method, wherein the protein in the specimen derived from the living body is at least one type selected from the group consisting of hemoglobin, haptoglobin, and a hemoglobin-haptoglobin complex.

(20) The method according to (19), wherein
the specimen derived from the living body contains at least hemoglobin, and
the hemoglobin in the sample forms a complex together with haptoglobin.

(21) The method according to (20), wherein the stabilizing solution is the stabilizing solution according to (16).

(22) A kit for detecting a protein contained in a specimen derived from a living body, the kit including:
the stabilizing solution according to (11) to (18); and
a reagent containing an antibody that recognizes the protein, wherein
the protein is at least one type selected from the group consisting of hemoglobin, haptoglobin, and a hemoglobin-haptoglobin complex.

Advantageous Effect of the Invention

According to the present invention, the protein such as blood protein contained in the specimen derived from a living body can be stabilized. In other words, according to the present invention, it is possible to prevent denaturation, decomposition, or modification of the protein such as blood protein contained in the specimen derived from a living body. According to the present invention, therefore, it is possible to accurately measure the protein contained in the specimen derived from a living body by an immunological measurement method.

EMBODIMENTS FOR CARRYING OUT THE INVENTION

Hereinafter, one or more preferred embodiments of the present invention will be described.
(Method of Stabilizing Protein Contained in Specimen Derived From Living Body and Stabilizing Solution For Protein)

The method of stabilizing a protein contained in a specimen derived from a living body according to an embodiment of the present invention includes a step of causing a protein contained in the specimen derived from a living body to coexist with an arylboronic acid. In the present embodiment, the protein contained in the specimen derived from a living body may be at least one type selected from the group consisting of hemoglobin, haptoglobin, and a hemoglobin-haptoglobin complex.

By causing the protein contained in the specimen derived from a living body to coexist with an arylboronic acid, the stability of the protein contained in the specimen derived from the living body can be enhanced. The protein-containing specimen derived from a living body may be feces, saliva, or urine and may be feces.

The method of causing the protein contained in the specimen derived from a living body to coexist with an arylboronic acid is not particularly limited, but examples of the method include a method of dispersing the protein contained in the specimen derived from a living body in a solution containing an arylboronic acid. Here, "dispersion" includes dissolution and suspension.

Examples of the solution containing an arylboronic acid include a preservation solution for preserving the specimen derived from a living body, a diluent solution for further diluting a sample in which the specimen is dispersed in a preservation solution, and a reaction solution in a kit or the like for detecting a protein in the specimen. In particular, the preservation solution for a specimen can be preferably used because it can significantly improve the stability of a protein contained in the specimen derived from a living body according to the present embodiment.

The arylboronic acid can be appropriately selected from known ones. The arylboronic acid may be at least one type selected from the group consisting of phenylboronic acid and derivatives thereof, may be at least one type selected from the group consisting of phenylboronic acid, hydroxyphenylboronic acid, carboxyphenylboronic acid, aminophenylboronic acid, and salts thereof, may be at least one type selected from the group consisting of phenylboronic acid, 3-hydroxyphenylboronic acid, 2-carboxyphenylboronic acid, 3-carboxyphenylboronic acid, 4-carboxyphenylboronic acid, 3-aminophenylboronic acid, and salts thereof, and may particularly be at least one type selected from the group consisting of phenylboronic acid, 3-hydroxyphenylboronic acid, 3-carboxyphenylboronic acid, 3-aminophenylboronic acid, and salts thereof.

The lower limit of the concentration of the arylboronic acid in the above solution may be preferably 0.1 mmol/L or more, 0.2 mmol/L or more, or 0.5 mmol/L or more. When the concentration of the arylboronic acid is the above lower limit or more, the effect of stabilizing the protein contained in the specimen derived from a living body is more excellent.

From another aspect, the upper limit of the concentration of the arylboronic acid in the above solution may be preferably 100 mmol/L or less, 50 mmol/L or less, or 30 mmol/L or less. If the concentration of the arylboronic acid is unduly high, the apparent recovery ratio may decrease when the protein contained in the specimen derived from a living body is measured by an immunological measurement method. This appears because the stabilizing effect of the protein contained in the specimen derived from the living body does not decrease, but the high concentration of arylboronic acid adversely effects the immunological measurement. Fortunately, however, when the concentration of the arylboronic acid is the above upper limit or less, the adverse effects on the immunological measurement method are suppressed, and more accurate measurement can be performed.

It is to be noted, however, that even when the solution contains a high concentration of arylboronic acid, if it coexists with a high concentration of sugar, which will be described later, the arylboronic acid and the sugar form a complex thereby to suppress the adverse effects on the immunological measurement method due to the high concentration of arylboronic acid. Thus, provided that the arylboronic acid coexists with a high concentration of sugar, even when the concentration of the arylboronic acid is about 50 mmol/L or further about 100 mmol/L, accurate measurement by the immunological measurement method is ensured.

In a more specific aspect of the present embodiment, the arylboronic acid can be contained in a solution (stabilizing solution) for stabilizing the protein contained in the specimen derived from a living body. For example, when the stabilizing solution does not contain haptoglobin, which will be described later, the lower limit of the concentration of the arylboronic acid in the stabilizing solution can be 0.1 mmol/L or more, 0.2 mmol/L or more, or 0.5 mmol/L or more. From another aspect, the upper limit of the concentration of the arylboronic acid in the stabilizing solution can be 20 mmol/L or less, 10 mmol/L or less, or 5 mmol/L or less.

The above step can be a step of causing the protein contained in the specimen derived from a living body to coexist with a sugar together with the above arylboronic acid. By coexisting with a sugar in addition to the arylboronic acid, the stability of the protein contained in the specimen derived from a living body can be further enhanced. Examples of the method of causing the protein contained in the specimen derived from a living body to coexist with a sugar include a method of causing the sugar to be further contained in a solution that contains the above arylboronic acid.

The sugar can be appropriately selected from known ones, and examples of the sugar include sugar alcohols such as sorbitol, mannitol, xylitol, and erythritol; monosaccharides such as glucose, fructose, mannose, and galactose; disaccharides such as sucrose, trehalose, lactose, and maltose; and oligosaccharide.

The sugar may be at least one type selected from the group consisting of sugar alcohols, monosaccharides, and disaccharides, may be at least one type selected from the group consisting of sorbitol, glucose, mannitol, fructose, xylitol, erythritol, sucrose, trehalose, lactose, and maltose, and may be at least one type selected from the group consisting of sorbitol, mannitol, fructose, and sucrose.

However, sugars (reducing sugars) such as glucose and fructose that form aldehyde groups or ketone groups in a solution react with proteins contained in the specimen derived from a living body or with albumins or the like added to the solution as stabilizers for these proteins (Maillard reaction) to modify the proteins and generate a brown substance (melanoidin) and, therefore, a sugar that does not react with proteins may be preferred. If the epitope or its vicinity of a protein contained in the specimen derived from a living body is modified by a reducing sugar to change the structure, some antibodies cannot recognize such proteins contained in the specimen derived from a living body, so that accurate measurement by an immunological measurement method may not be possible. In a more specific aspect of the present embodiment, therefore, it is more preferred to use a non-reducing sugar that does not react with proteins. The non-reducing sugar may be at least one type selected from the group consisting of sorbitol, mannitol, xylitol, erythritol, trehalose, sucrose, and lactose, and may be at least one type selected from the group consisting of sorbitol, mannitol, and sucrose.

The lower limit of the sugar concentration may be preferably 5 mmol/L or more, 10 mmol/L or more, or 25 mmol/L or more. When the sugar concentration is the above lower limit or more, the sugar acts synergistically with an arylboronic acid, and the effect of stabilizing the protein contained in the specimen derived from a living body is further excellent.

The upper limit of the sugar concentration may be 1000 mmol/L or less, 500 mmol/L or less, or 100 mmol/L or less for sugar alcohols and monosaccharides, and may be 500 mmol/L or less, 250 mmol/L or less, or 100 mmol/L or less for disaccharides. When the sugar concentration is the above upper limit or less, the viscosity of the stabilizing solution is not unduly high, so the measurement may be performed without any problem.

It suffices that the stabilizing solution for preserving the protein contained in the specimen derived from a living body is a buffer solution that can keep the pH at 5 to 10 or preferably 6 to 8, and the stabilizing solution may be a buffer solution that contains a Good buffer such as 2-morpholino-ethanesulfonic acid (MES), hydroxyethylpiperazine-2-ethanesulfonic acid (HEPES), or piperazine-bis(2-ethanesulfonic acid) (PIPES), and may be a phosphate buffer solution, a tris buffer solution, or a glycine buffer solution.

The stabilizing solution may further contain additives such as an antibacterial agent, a pH adjuster, a salt for adjusting the ionic strength, a surfactant, an agglutination promoter, and a known stabilizing agent used when preserving proteins. Examples of the antibacterial agent include sodium azide, an antibiotic, and a lytic enzyme. Examples of the additives include known substances that are known to have a protein stabilizing action, such as histidine, lysine, and other amino acids, albumin, a protease inhibitor, and ethylenediaminetetraacetic acid (EDTA) and other chelating agents.

According to the above-described stabilizing method or stabilizing solution, the stability of the protein contained in the specimen derived from a living body can be enhanced by the action of the arylboronic acid or the synergistic action of the arylboronic acid and the sugar. In other words, according to the above-described stabilizing method or stabilizing solution, it is possible to prevent denaturation, decomposition, or modification of the protein contained in the specimen derived from a living body and maintain the structure of the epitope and its surrounding region of the protein contained in the specimen derived from the living body. Thus, when detecting the protein contained in the specimen derived from a living body by an immunological measurement method, improvement in the detection accuracy can be expected.

A more specific aspect of the present embodiment may include a step of bringing the specimen derived from a living body containing at least hemoglobin into contact with haptoglobin thereby to form a hemoglobin-haptoglobin complex. In this case, the specimen derived from a living body containing hemoglobin may be feces, saliva, or urine and may be feces. The method of the present embodiment is distinctly useful because feces contain a particularly considerable number of bacteria and enzymes that cause decomposition and modification of hemoglobin.

The specimen derived from a living body containing hemoglobin may be brought into contact with the haptoglobin in any manner, but it may be preferred to add the specimen derived from a living body containing hemoglobin to the previously described preservation solution containing haptoglobin. Hemoglobin contained in the specimen derived from a living body rapidly reacts with the haptoglobin in the preservation solution to form a hemoglobin-haptoglobin complex. Then, the preservation solution to which the specimen derived from a living body is added may be preserved without any treatment, and the hemoglobin-haptoglobin complex can thereby be stably preserved. In the formation of a complex of hemoglobin and haptoglobin, the hemoglobin dissociates from a tetramer ($\alpha2\beta2$) having two $\alpha$ chains and two $\beta$ chains associated with each other into two dimers ($\alpha\beta$), but this phenomenon does not represent the "decomposition" or "denaturation" in the present specification.

The stabilizing solution for stabilizing the protein contained in the specimen derived from a living body containing hemoglobin according to the present embodiment may preferably be a solution obtained by further adding haptoglobin to the above-described stabilizing solution which contains an arylboronic acid or contains an arylboronic acid and a sugar. The concentration of haptoglobin in the stabilizing solution depends on the amount of the specimen derived from a living body, but may be, for example, 0.05 units/L to 50 units/L, 0.1 units/L to 10 units/L, or 0.2 units/L to 2 units/L. Here, one unit represents the amount of haptoglobin that binds to 1 mg of hemoglobin. The haptoglobin concentration in the above range is a concentration sufficient to convert all hemoglobin in the specimen derived from a living body into a hemoglobin-haptoglobin complex.

Here, when the stabilizing solution contains haptoglobin, which will be described later, the lower limit of the concentration of the above arylboronic acid in the stabilizing solution can be 0.1 mmol/L or more, 0.2 mmol/L or more, 0.5 mmol/L or more, 1 mmol/L or more, or 5 mmol/L or more. When the concentration of the arylboronic acid is the above lower limit or more, the stabilizing effect of the arylboronic acid on the hemoglobin contained in the specimen derived from a living body is more remarkable in corporation with the stabilizing effect of the haptoglobin.

From another aspect, the upper limit of the concentration of the arylboronic acid in the stabilizing solution can be 100 mmol/L or less, 50 mmol/L or less, or 30 mmol/L or less. When the concentration of the arylboronic acid is the above upper limit or less, adverse effects on an immunological measurement method are suppressed, and more accurate measurement is possible.

According to the stabilizing method or stabilizing solution of the above-described aspect, the hemoglobin contained in the specimen derived from a living body can be stably preserved in the form of a hemoglobin-haptoglobin complex. In other words, according to the above-described stabilizing method or stabilizing solution, it is possible to prevent denaturation, decomposition, or modification of the hemoglobin contained in the specimen derived from a living body and maintain the structure of the epitope and its surrounding region of the hemoglobin. Thus, when measuring the hemoglobin contained in the specimen derived from a living body by an immunological measurement method, improvement in the detection accuracy can be expected.

(Method of Detecting Protein Contained in Specimen Derived From Living Body and Detection Kit)

The method of detecting a protein contained in the specimen derived from a living body, which is provided by an embodiment of the present invention, includes a step of adding the specimen derived from the living body to the above-described stabilizing solution for stabilizing the protein to obtain a sample containing the specimen derived from the living body and a step of detecting the protein in the sample by an immunological measurement method.

The kit for detecting a protein contained in the specimen derived from a living body, which is provided by another embodiment of the present invention, includes the above-described stabilizing solution and a reagent containing an antibody that recognizes the protein contained in the specimen derived from the living body.

In the above detection method or detection kit, the protein contained in the specimen derived from the living body may be at least one type selected from hemoglobin, haptoglobin, and a hemoglobin-haptoglobin complex.

Examples of the stabilizing solution used in the present embodiment include a preservation solution for preserving the specimen derived from a living body, a diluent solution for further diluting a sample in which the specimen is dispersed in a preservation solution, and a reaction solution in a kit or the like for detecting the protein in the specimen. Examples of the reaction solution in a kit or the like include a solution containing an antibody in an immunological measurement method, which will be described later, and a solution for being mixed with a sample to adjust the measurement environment.

The immunological measurement method is a method utilizing an antibody which reacts with a protein contained in the specimen derived from a living body, and a known immunological measurement method can be used. The immunological measurement method may be, for example, an immunoagglutination method such as a latex agglutination method or a gold colloid agglutination method, an immunochromatography method, or an ELISA method.

The antibody reacting with the protein contained in the specimen derived from a living body may be, but is not limited to, a polyclonal antibody, a monoclonal antibody, or a fragment of an antibody reacting with the protein contained in the specimen derived from a living body, which fragment is capable of recognizing the protein contained in the specimen derived from the living body.

It suffices that the antibody reacting with the protein contained in the specimen derived from a living body is an antibody that recognizes the protein to be measured, and the antibody may be an anti-hemoglobin antibody, an anti-haptoglobin antibody, or an anti-hemoglobin-haptoglobin complex antibody. These antibodies can be made by commonly-used methods.

As an example, detection of the protein contained in the specimen derived from a living body, such as detection of hemoglobin, can be performed as follows. First, the specimen is added to a container containing a preservation solution to prepare a sample. The specimen may be preserved in the container for an arbitrary time, or the preservation solution containing the specimen may be filtered to prepare a sample. Then, the hemoglobin in the sample is detected by an immunological measurement method such as a latex agglutination method. More specifically, a reagent containing latex particles having surfaces immobilizing an anti-hemoglobin antibody is added to the sample. Before adding the reagent containing the latex particles, the sample may be diluted with a diluent, or a reaction solution may be added. In the present aspect, the above-described stabilizing solution containing an arylboronic acid may be any of a preservation solution, a diluent solution, and a reaction solution. It is particularly preferred that the preservation solution be the above-described stabilizing solution. In this case, the diluent solution and/or reaction solution may or may not contain an arylboronic acid.

In the specimen derived from a living body, hemoglobin may form a complex together with haptoglobin in the specimen or may exist as free hemoglobin. Thus, preferably, the anti-hemoglobin antibody used for the detection of hemoglobin is capable of recognizing the epitope of the free hemoglobin and the epitope of hemoglobin in the hemoglobin-haptoglobin complex and does not cross-react with haptoglobin.

When hemoglobin exists in a sample, the anti-hemoglobin antibody recognizes the hemoglobin, and the latex particles immobilizing the antibody agglutinate. The change in turbidity due to agglutination is measured, and the hemoglobin concentration in the sample may be obtained from the calibration curve created using a calibrator that contains hemoglobin of a known concentration. Additionally or alternatively, the concentration of hemoglobin in the sample can be obtained from the calibration curve created based on the concentration of hemoglobin in the calibrator.

When the above stabilizing solution contains haptoglobin, detection of hemoglobin can be performed, for example, as follows. First, the specimen is added to a container containing a preservation solution to prepare a sample. The specimen may be preserved in the container for an arbitrary time, or the preservation solution containing the specimen may be filtered to prepare a sample. Then, the hemoglobin in the sample is detected by an immunological measurement method such as a latex agglutination method. More specifically, a reagent containing latex particles having surfaces immobilizing an anti-hemoglobin antibody is added to the sample. Before adding the reagent containing the latex particles, the sample may be diluted with a diluent, or a reaction solution may be added.

In the present aspect, the stabilizing solution containing an arylboronic acid and haptoglobin may be any of a preservation solution, a diluent solution, and a reaction solution.

It is particularly preferred that the preservation solution be the stabilizing solution containing an arylboronic acid and haptoglobin. In this case, the diluent solution and/or reaction solution may or may not contain haptoglobin and may or may not contain an arylboronic acid.

In the present aspect, when hemoglobin exists in the specimen, the hemoglobin reacts with haptoglobin contained in the stabilizing solution to form a hemoglobin-haptoglobin complex. It is not necessary for all hemoglobin in the specimen to form a complex, and hemoglobin that does not form a complex together with haptoglobin may exist in the stabilizing solution (sample) containing the specimen (the preservation solution containing a specimen will be referred to as a sample herein), but preferably, all hemoglobin in the specimen forms a complex together with haptoglobin.

Preferably, the anti-hemoglobin antibody is capable of recognizing the epitope of hemoglobin in the hemoglobin-haptoglobin complex and does not cross-react with haptoglobin.

When hemoglobin exists in the sample, the anti-hemoglobin antibody recognizes the hemoglobin (including hemoglobin that forms a complex with haptoglobin), and the latex particles immobilizing the antibody agglutinate. The change in turbidity due to agglutination is measured, and the hemoglobin concentration in the sample may be obtained from the calibration curve created using a calibrator that contains a hemoglobin-haptoglobin complex of a known hemoglobin concentration. Additionally or alternatively, the concentration of the hemoglobin-haptoglobin complex in the sample can be obtained from the calibration curve created based on the concentration of the hemoglobin-haptoglobin complex in the calibrator.

It should be appreciated that the embodiments heretofore explained are described to facilitate understanding of the present invention and are not described to limit the present invention. It is therefore intended that the elements disclosed in the above embodiments include all design changes and equivalents to fall within the technical scope of the present invention.

EXAMPLES

Example 1

Preservation solutions were prepared with the addition of 40 mmol/L HEPES (pH 6.8), 0.1% BSA, 0.1% $NaN_3$, 1 unit/L haptoglobin, and 0 to 100 mmol/L phenylboronic acid. Samples obtained by adding hemoglobin-added fecal specimens to the preservation solutions so that the fecal concentration would be 0.5% were preserved at 37° C. for 0, 7, 14, and 21 days. The fecal specimens were added with hemoglobin having an amount such that the hemoglobin concentration in the samples would be about 300 µg/L. Instead of the fecal specimens to which hemoglobin was added, samples containing no fecal specimens, in which hemoglobin was added to the preservation solutions so that the hemoglobin concentration in the samples would be 300 µg/L, were similarly preserved. The hemoglobin (Hb) concentrations (µg/L) in the preserved samples were measured by the latex agglutination method.

The concentrations of hemoglobin were measured using "OC-Hemodia (registered trademark) Auto III 'EIKEN'" (available from EIKEN CHEMICAL CO., LTD.) as a measurement reagent and "OC-sensor DIANA" (available from EIKEN CHEMICAL CO., LTD.) as a measurement device. The above measurement reagent contains latex particles immobilizing an anti-human hemoglobin rabbit polyclonal antibody.

From the measured concentrations of hemoglobin, the recovery ratios (%) were calculated with respect to the hemoglobin concentrations immediately after the fecal specimens were added to the preservation solutions (i.e., concentrations 0 days after the fecal specimens were added). The results are listed in Table 1. As clearly understood from Table 1, in any of samples of Feces 1, Feces 2, and Feces 3, the recovery ratio of hemoglobin in the samples was improved by adding phenylboronic acid at a concentration of 0.5 mmol/L or more. The recovery ratio of hemoglobin was improved depending on the phenylboronic acid concentration and reached the maximum at a phenylboronic acid concentration of 15 mmol/L, and the apparent recovery ratio decreased with the addition of 50 mmol/L or more. In the samples containing no fecal specimens, the improvement of recovery ratio by addition of phenylboronic acid was not observed. These results indicate that the phenylboronic acid stabilizes the hemoglobin in the samples containing feces. The hemoglobin in the samples exists as a hemoglobin-haptoglobin complex react to haptoglobin contained in the preservation solution; therefore, the above results mean that the phenylboronic acid stabilized the hemoglobin-haptoglobin complex.

TABLE 1

| | Phenyl-boronic acid (mmol/L) | Hb concentration (µg/L) Number of days for preservation at 37° C. | | | | Recovery ratio with respect to Hb concentration after 0 days (%) Number of days for preservation at 37° C. | | | |
|---|---|---|---|---|---|---|---|---|---|
| | | 0 days | 7 days | 14 days | 21 days | 0 days | 7 days | 14 days | 21 days |
| Feces 1 | 0 | 282 | 135 | 99 | 71 | 100 | 48 | 35 | 25 |
| | 0.5 | 279 | 181 | 147 | 129 | 100 | 65 | 53 | 46 |
| | 1 | 275 | 182 | 148 | 125 | 100 | 66 | 54 | 45 |
| | 2.5 | 289 | 207 | 175 | 152 | 100 | 72 | 61 | 53 |
| | 15 | 302 | 243 | 239 | 224 | 100 | 80 | 79 | 74 |
| | 50 | 290 | 230 | 204 | 185 | 100 | 79 | 70 | 64 |
| | 100 | 271 | 186 | 137 | 97 | 100 | 69 | 51 | 36 |
| Feces 2 | 0 | 292 | 111 | 68 | 50 | 100 | 38 | 23 | 17 |
| | 0.5 | 271 | 147 | 113 | 91 | 100 | 54 | 42 | 34 |
| | 1 | 284 | 166 | 136 | 116 | 100 | 58 | 48 | 41 |
| | 2.5 | 288 | 195 | 159 | 139 | 100 | 68 | 55 | 48 |
| | 15 | 283 | 249 | 214 | 191 | 100 | 88 | 76 | 67 |
| | 50 | 269 | 214 | 174 | 149 | 100 | 80 | 65 | 55 |
| | 100 | 250 | 139 | 80 | 36 | 100 | 56 | 32 | 14 |
| Feces 3 | 0 | 286 | 93 | 60 | 51 | 100 | 33 | 21 | 18 |
| | 0.5 | 283 | 133 | 104 | 93 | 100 | 47 | 37 | 33 |
| | 1 | 281 | 159 | 131 | 115 | 100 | 57 | 47 | 41 |
| | 2.5 | 290 | 189 | 160 | 145 | 100 | 65 | 55 | 50 |
| | 15 | 288 | 224 | 200 | 185 | 100 | 78 | 69 | 64 |
| | 50 | 274 | 204 | 176 | 158 | 100 | 74 | 64 | 58 |
| | 100 | 247 | 156 | 88 | 53 | 100 | 63 | 36 | 21 |
| No feces | 0 | 268 | 243 | 238 | 239 | 100 | 91 | 89 | 89 |
| | 0.5 | 257 | 248 | 243 | 246 | 100 | 96 | 95 | 96 |
| | 1 | 265 | 244 | 241 | 244 | 100 | 92 | 91 | 92 |
| | 2.5 | 272 | 249 | 244 | 258 | 100 | 92 | 90 | 95 |
| | 15 | 286 | 262 | 253 | 264 | 100 | 92 | 88 | 92 |
| | 50 | 260 | 242 | 228 | 235 | 100 | 93 | 88 | 90 |
| | 100 | 239 | 198 | 183 | 178 | 100 | 83 | 77 | 74 |

Example 2

Preservation solutions were prepared by adding 2-carboxyphenylboronic acid (2-CPBA), 3-carboxyphenylboronic acid (3-CPBA), 4-carboxyphenylboronic acid (4-CPBA), 3-hydroxyphenylboronic acid (3-HPBA), and 3-aminophenylboronic acid (3-APBA) each at 15 mmol/L as substitute for the phenylboronic acid in the preservation solutions of Example 1, and testing was conducted in the same manner as in Example 1. For comparative examples, preservation solutions to which no arylboronic acid was added were prepared, and testing was conducted in the same manner. The results are listed in Table 2. As clearly understood from Table 2, also when other arylboronic acids were used, the recovery ratio of hemoglobin in the sample was improved in any of fecal specimens of Feces 1, Feces 2, and Feces 3 as compared with the comparative examples in which no arylboronic acid was added.

TABLE 2

| | Arylboronic acid (15 mmol/L) | Hb concentration (μg/L) Number of days for preservation at 37° C. | | | Recovery ratio with respect to Hb after 0 days (%) Number of days for preservation at 37° C. | | |
|---|---|---|---|---|---|---|---|
| | | 0 days | 7 days | 14 days | 0 days | 7 days | 14 days |
| Feces 1 | No addition | 315 | 154 | 119 | 100 | 49 | 38 |
| | 2C-PBA | 315 | 196 | 150 | 100 | 62 | 48 |
| | 3C-PBA | 309 | 249 | 239 | 100 | 81 | 77 |
| | 4C-PBA | 312 | 252 | 234 | 100 | 81 | 75 |
| | 3H-PBA | 327 | 269 | 268 | 100 | 82 | 82 |
| | 3A-PBA | 339 | 275 | 260 | 100 | 81 | 77 |
| Feces 2 | No addition | 313 | 108 | 78 | 100 | 34 | 25 |
| | 2C-PBA | 311 | 157 | 103 | 100 | 50 | 33 |
| | 3C-PBA | 309 | 264 | 240 | 100 | 85 | 78 |
| | 4C-PBA | 315 | 239 | 227 | 100 | 76 | 72 |
| | 3H-PBA | 326 | 227 | 264 | 100 | 85 | 81 |
| | 3A-PBA | 330 | 287 | 261 | 100 | 87 | 79 |
| Feces 3 | No addition | 304 | 90 | 63 | 100 | 30 | 21 |
| | 2C-PBA | 300 | 124 | 76 | 100 | 41 | 25 |
| | 3C-PBA | 300 | 213 | 200 | 100 | 71 | 67 |
| | 4C-PBA | 300 | 219 | 194 | 100 | 73 | 65 |
| | 3H-PBA | 313 | 213 | 206 | 100 | 68 | 66 |
| | 3A-PBA | 324 | 227 | 209 | 100 | 70 | 64 |
| No feces | No addition | 295 | 276 | 267 | 100 | 94 | 91 |
| | 2C-PBA | 292 | 272 | 264 | 100 | 93 | 90 |
| | 3C-PBA | 293 | 281 | 276 | 100 | 96 | 94 |
| | 4C-PBA | 279 | 275 | 271 | 100 | 98 | 97 |
| | 3H-PBA | 303 | 294 | 296 | 100 | 97 | 98 |
| | 3A-PBA | 278 | 275 | 272 | 100 | 99 | 98 |

Example 3

The concentration of phenylboronic acid in the preservation solutions of Example 1 was fixed to 15 mmol/L, preservation solutions to which a sugar (sorbitol, sucrose, trehalose, glucose, fructose, or mannitol) was further added at 50 mmol/L or 100 mmol/L or preservation solutions to which no sugar was added were prepared, and testing was conducted in the same manner as in Example 1. For comparative examples, preservation solutions to which the phenylboronic acid and sugar were not added were prepared, and testing was conducted in the same manner. The results are listed in Table 3. As clearly understood from Table 3, when sorbitol, mannitol, sucrose, or fructose was further added to the phenylboronic acid, the recovery ratio of hemoglobin in the sample was further improved in any of fecal specimens of Feces 1, Feces 2, and Feces 3 and remarkably improved particularly with any of sorbitol and mannitol. With trehalose or glucose, however, fecal specimens (Feces 3) in which the recovery ratios were not improved were also recognized. These results indicate that the stability of hemoglobin in the samples containing feces can be further improved by adding a sugar to the phenylboronic acid, but the effects differ depending on the type of a sugar added. Among sorbitol, sucrose, trehalose, glucose, fructose, and mannitol, the sorbitol and mannitol had remarkable effects, and in particular, the sorbitol exhibited no decrease in the recovery ratios in the fecal specimens (Feces 1).

TABLE 3

| | Phenyl-boronic acid (mmol/L) | Sugar (mmol/L) | | Hb concentration (μg/L) Number of days for preservation at 37° C. | | | | Recovery ratio with respect to Hb concentration after 0 days (%) Number of days for preservation at 37° C. | | | |
|---|---|---|---|---|---|---|---|---|---|---|---|
| | | | | 0 days | 7 days | 14 days | 21 days | 0 days | 7 days | 14 days | 21 days |
| Feces 1 | No addition | No addition | | 282 | 135 | 99 | 71 | 100 | 48 | 35 | 25 |
| | 15 | No addition | | 302 | 243 | 239 | 224 | 100 | 80 | 79 | 74 |
| | | Sorbitol | 50 | 291 | 300 | 300 | 296 | 100 | 103 | 103 | 102 |
| | | | 100 | 287 | 292 | 294 | 290 | 100 | 102 | 102 | 101 |
| | | Sucrose | 50 | 291 | 281 | 274 | 268 | 100 | 97 | 94 | 92 |
| | | | 100 | 286 | 272 | 270 | 258 | 100 | 95 | 94 | 90 |
| | | Trehalose | 50 | 299 | 261 | 247 | 241 | 100 | 87 | 83 | 81 |
| | | | 100 | 291 | 249 | 238 | 230 | 100 | 86 | 82 | 79 |
| | | Glucose | 50 | 283 | 255 | 242 | 239 | 100 | 90 | 86 | 84 |
| | | | 100 | 291 | 251 | 236 | 230 | 100 | 86 | 81 | 79 |
| | | Fructose | 50 | 297 | 294 | 285 | 280 | 100 | 99 | 96 | 94 |
| | | | 100 | 287 | 276 | 247 | 228 | 100 | 96 | 86 | 79 |
| | | Mannitol | 50 | 288 | 278 | 270 | — | 100 | 96 | 94 | — |
| | | | 100 | 281 | 279 | 276 | — | 100 | 99 | 98 | — |

TABLE 3-continued

| | Phenyl-boronic acid (mmol/L) | Sugar (mmol/L) | | Hb concentration (µg/L) Number of days for preservation at 37° C. | | | | Recovery ratio with respect to Hb concentration after 0 days (%) Number of days for preservation at 37° C. | | | |
|---|---|---|---|---|---|---|---|---|---|---|---|
| | | | | 0 days | 7 days | 14 days | 21 days | 0 days | 7 days | 14 days | 21 days |
| Feces 2 | No addition | No addition | | 292 | 111 | 68 | 50 | 100 | 38 | 23 | 17 |
| | 15 | No addition | | 283 | 249 | 214 | 191 | 100 | 88 | 76 | 67 |
| | | Sorbitol | 50 | 281 | 280 | 252 | 222 | 100 | 100 | 90 | 79 |
| | | | 100 | 274 | 276 | 246 | 219 | 100 | 101 | 90 | 80 |
| | | Sucrose | 50 | 273 | 266 | 232 | 212 | 100 | 97 | 85 | 78 |
| | | | 100 | 267 | 257 | 236 | 219 | 100 | 96 | 88 | 82 |
| | | Trehalose | 50 | 284 | 257 | 223 | 201 | 100 | 90 | 79 | 71 |
| | | | 100 | 269 | 251 | 227 | 206 | 100 | 93 | 84 | 77 |
| | | Glucose | 50 | 275 | 260 | 230 | 205 | 100 | 95 | 84 | 75 |
| | | | 100 | 281 | 246 | 223 | 203 | 100 | 88 | 79 | 72 |
| | | Fructose | 50 | 270 | 275 | 243 | 222 | 100 | 102 | 90 | 82 |
| | | | 100 | 280 | 264 | 235 | 212 | 100 | 94 | 84 | 76 |
| | | Mannitol | 50 | 296 | 291 | 280 | — | 100 | 98 | 95 | — |
| | | | 100 | 290 | 290 | 286 | — | 100 | 100 | 99 | — |
| Feces 3 | No addition | No addition | | 286 | 93 | 60 | 51 | 100 | 33 | 21 | 18 |
| | 15 | No addition | | 288 | 224 | 200 | 185 | 100 | 78 | 69 | 64 |
| | | Sorbitol | 50 | 283 | 250 | 235 | 223 | 100 | 88 | 83 | 79 |
| | | | 100 | 278 | 244 | 226 | 219 | 100 | 88 | 81 | 79 |
| | | Sucrose | 50 | 286 | 234 | 209 | 195 | 100 | 82 | 73 | 68 |
| | | | 100 | 272 | 230 | 201 | 187 | 100 | 85 | 74 | 69 |
| | | Trehalose | 50 | 282 | 221 | 197 | 178 | 100 | 78 | 70 | 63 |
| | | | 100 | 281 | 213 | 192 | 179 | 100 | 76 | 68 | 64 |
| | | Glucose | 50 | 285 | 217 | 196 | 184 | 100 | 76 | 69 | 65 |
| | | | 100 | 276 | 210 | 188 | 174 | 100 | 76 | 68 | 63 |
| | | Fructose | 50 | 272 | 238 | 218 | 203 | 100 | 88 | 80 | 75 |
| | | | 100 | 276 | 244 | 222 | 204 | 100 | 88 | 80 | 74 |
| | | Mannitol | 50 | 293 | 247 | 238 | — | 100 | 84 | 81 | — |
| | | | 100 | 286 | 243 | 240 | — | 100 | 85 | 84 | — |
| No feces | No addition | No addition | | 268 | 243 | 238 | 239 | 100 | 91 | 89 | 89 |
| | 15 | No addition | | 286 | 262 | 253 | 264 | 100 | 92 | 88 | 92 |
| | | Sorbitol | 50 | 281 | 261 | 251 | 265 | 100 | 93 | 89 | 94 |
| | | | 100 | 276 | 252 | 244 | 255 | 100 | 91 | 88 | 92 |
| | | Sucrose | 50 | 271 | 253 | 246 | 257 | 100 | 93 | 91 | 95 |
| | | | 100 | 267 | 247 | 241 | 260 | 100 | 93 | 90 | 97 |
| | | Trehalose | 50 | 268 | 253 | 255 | 257 | 100 | 94 | 95 | 96 |
| | | | 100 | 269 | 248 | 251 | 251 | 100 | 92 | 93 | 93 |
| | | Glucose | 50 | 282 | 254 | 263 | 260 | 100 | 90 | 93 | 92 |
| | | | 100 | 266 | 251 | 253 | 257 | 100 | 94 | 95 | 97 |
| | | Fructose | 50 | 286 | 255 | 261 | 275 | 100 | 89 | 91 | 96 |
| | | | 100 | 281 | 245 | 251 | 262 | 100 | 87 | 89 | 93 |
| | | Mannitol | 50 | 270 | 263 | 254 | — | 100 | 98 | 94 | — |
| | | | 100 | 269 | 260 | 252 | — | 100 | 97 | 94 | — |

Example 4

Preservation solutions in which sorbitol, sucrose, trehalose, glucose, fructose, or mannitol was added at 100 mmol/L to the preservation solutions of Example 1 containing no phenylboronic acid were prepared, and testing was conducted in the same manner as in Example 1. For comparison, the same testing was conducted without adding these sugars. The results are listed in Table 4. As clearly understood from Table 4, addition of sorbitol, sucrose, trehalose, glucose, or fructose to the preservation solutions containing no phenylboronic acid does not improve the recovery ratio of hemoglobin in the samples containing fecal specimens. This result indicates that a sugar such as sorbitol, sucrose, trehalose, glucose, or fructose alone does not stabilize the hemoglobin in the samples containing feces and also indicates that the phenylboronic acid and a sugar have to exist together.

TABLE 4

| | Phenyl-boronic acid | Sugar (100 mmol/L) | Hb concentration (µg/L) Number of days for preservation at 37° C. | | | | Recovery ratio with respect to Hb concentration after 0 days (%) Number of days for preservation at 37° C. | | | |
|---|---|---|---|---|---|---|---|---|---|---|
| | | | 0 days | 7 days | 14 days | 21 days | 0 days | 7 days | 14 days | 21 days |
| Feces 1 | No addition | No addition | 282 | 135 | 99 | 71 | 100 | 48 | 35 | 25 |
| | | Sorbitol | 283 | 143 | 102 | 97 | 100 | 51 | 36 | 34 |
| | | Sucrose | 264 | 115 | 70 | 80 | 100 | 44 | 27 | 30 |
| | | Trehalose | 266 | 121 | 80 | 44 | 100 | 45 | 30 | 17 |
| | | Glucose | 276 | 135 | 99 | 59 | 100 | 49 | 36 | 21 |
| | | Fructose | 285 | 127 | 85 | 81 | 100 | 45 | 30 | 28 |
| | | Mannitol | 276 | 156 | 130 | — | 100 | 57 | 47 | — |

TABLE 4-continued

| | Phenyl-boronic acid | Sugar (100 mmol/L) | Hb concentration (μg/L) Number of days for preservation at 37° C. | | | | Recovery ratio with respect to Hb concentration after 0 days (%) Number of days for preservation at 37° C. | | | |
|---|---|---|---|---|---|---|---|---|---|---|
| | | | 0 days | 7 days | 14 days | 21 days | 0 days | 7 days | 14 days | 21 days |
| Feces 2 | No addition | No addition | 292 | 111 | 68 | 59 | 100 | 38 | 23 | 20 |
| | | Sorbitol | 277 | 113 | 77 | 51 | 100 | 41 | 28 | 18 |
| | | Sucrose | 270 | 96 | 49 | 31 | 100 | 36 | 18 | 11 |
| | | Trehalose | 264 | 106 | 61 | 41 | 100 | 40 | 23 | 16 |
| | | Glucose | 276 | 105 | 54 | 37 | 100 | 38 | 20 | 13 |
| | | Fructose | 273 | 100 | 56 | 35 | 100 | 37 | 21 | 13 |
| | | Mannitol | 284 | 97 | 81 | — | 100 | 34 | 28 | — |
| Feces 3 | No addition | No addition | 286 | 93 | 60 | 51 | 100 | 33 | 21 | 18 |
| | | Sorbitol | 278 | 98 | 62 | 56 | 100 | 35 | 22 | 20 |
| | | Sucrose | 267 | 89 | 55 | 40 | 100 | 33 | 21 | 15 |
| | | Trehalose | 267 | 91 | 56 | 47 | 100 | 34 | 21 | 18 |
| | | Glucose | 272 | 93 | 55 | 46 | 100 | 34 | 20 | 17 |
| | | Fructose | 265 | 83 | 41 | 39 | 100 | 31 | 15 | 15 |
| | | Mannitol | 282 | 93 | 78 | — | 100 | 33 | 28 | — |
| No feces | No addition | No addition | 268 | 243 | 238 | 239 | 100 | 91 | 89 | 89 |
| | | Sorbitol | 255 | 239 | 235 | 236 | 100 | 94 | 92 | 93 |
| | | Sucrose | 245 | 228 | 223 | 222 | 100 | 93 | 91 | 91 |
| | | Trehalose | 243 | 229 | 225 | 222 | 100 | 94 | 93 | 91 |
| | | Glucose | 245 | 231 | 223 | 223 | 100 | 94 | 91 | 91 |
| | | Fructose | 250 | 215 | 196 | 177 | 100 | 86 | 78 | 71 |
| | | Mannitol | 261 | 251 | 244 | — | 100 | 96 | 93 | — |

Example 5

The concentration of phenylboronic acid in the preservation solutions of Example 1 was fixed to 15 mmol/L, preservation solutions to which sorbitol was added at 10 to 500 mmol/L or sucrose was added at 10 to 250 mmol/L or preservation solutions to which no sugar was added were prepared, and testing was conducted in the same manner as in Example 1. For comparative examples, preservation solutions to which the phenylboronic acid and sugar were not added were prepared, and testing was conducted in the same manner. The results are listed in Table 5. As clearly understood from Table 5, in any of the samples of Feces 1, Feces 2, and Feces 3, the recovery ratio of hemoglobin in the samples containing feces was improved depending on the added concentration of sorbitol or sucrose and became constant with addition at 25 mmol/L or more.

TABLE 5

| | Phenyl-boronic acid (mmol/L) | Sugar (mmol/L) | | Hb concentration (μg/L) Number of days for preservation at 37° C. | | | | Recovery ratio with respect to Hb concentration after 0 days (%) Number of days for preservation at 37° C. | | | |
|---|---|---|---|---|---|---|---|---|---|---|---|
| | | | | 0 days | 7 days | 14 days | 21 days | 0 days | 7 days | 14 days | 21 days |
| Feces 1 | No addition | No addition | | 282 | 135 | 99 | 71 | 100 | 48 | 35 | 25 |
| | 15 | No addition | | 302 | 243 | 239 | 224 | 100 | 80 | 79 | 74 |
| | | Sorbitol | 10 | 305 | 280 | 269 | 259 | 100 | 92 | 88 | 85 |
| | | | 25 | 301 | 288 | 289 | 276 | 100 | 96 | 96 | 92 |
| | | | 50 | 291 | 300 | 300 | 296 | 100 | 103 | 103 | 102 |
| | | | 100 | 287 | 292 | 294 | 290 | 100 | 102 | 102 | 101 |
| | | | 500 | 251 | 251 | 256 | 251 | 100 | 100 | 102 | 100 |
| | | Sucrose | 10 | 304 | 273 | 264 | 249 | 100 | 90 | 87 | 82 |
| | | | 25 | 287 | 281 | 266 | 261 | 100 | 98 | 93 | 91 |
| | | | 50 | 291 | 281 | 274 | 268 | 100 | 97 | 94 | 92 |
| | | | 100 | 286 | 272 | 270 | 258 | 100 | 95 | 94 | 90 |
| | | | 250 | 258 | 250 | 241 | 232 | 100 | 97 | 93 | 90 |
| Feces 2 | No addition | No addition | | 292 | 111 | 68 | 50 | 100 | 38 | 23 | 17 |
| | 15 | No addition | | 283 | 249 | 214 | 191 | 100 | 88 | 76 | 67 |
| | | Sorbitol | 10 | 289 | 262 | 225 | 197 | 100 | 91 | 78 | 68 |
| | | | 25 | 283 | 277 | 245 | 213 | 100 | 98 | 87 | 75 |
| | | | 50 | 281 | 280 | 252 | 222 | 100 | 100 | 90 | 79 |
| | | | 100 | 274 | 276 | 246 | 219 | 100 | 101 | 90 | 80 |
| | | | 500 | 256 | 250 | 226 | 204 | 100 | 98 | 88 | 80 |
| | | Sucrose | 10 | 286 | 270 | 237 | 213 | 100 | 94 | 83 | 74 |
| | | | 25 | 287 | 274 | 241 | 223 | 100 | 95 | 84 | 78 |
| | | | 50 | 273 | 266 | 232 | 212 | 100 | 97 | 85 | 78 |
| | | | 100 | 267 | 257 | 236 | 219 | 100 | 96 | 88 | 82 |
| | | | 250 | 245 | 235 | 216 | 193 | 100 | 96 | 88 | 79 |

TABLE 5-continued

| | Phenyl-boronic acid (mmol/L) | Sugar (mmol/L) | | Hb concentration (μg/L) Number of days for preservation at 37° C. | | | | Recovery ratio with respect to Hb concentration after 0 days (%) Number of days for preservation at 37° C. | | | |
|---|---|---|---|---|---|---|---|---|---|---|---|
| | | | | 0 days | 7 days | 14 days | 21 days | 0 days | 7 days | 14 days | 21 days |
| Feces 3 | No addition | No addition | | 286 | 93 | 60 | 51 | 100 | 33 | 21 | 18 |
| | 15 | No addition | | 288 | 224 | 200 | 185 | 100 | 78 | 69 | 64 |
| | | Sorbitol | 10 | 279 | 233 | 210 | 201 | 100 | 84 | 75 | 72 |
| | | | 25 | 285 | 240 | 225 | 213 | 100 | 84 | 79 | 75 |
| | | | 50 | 283 | 250 | 235 | 223 | 100 | 88 | 83 | 79 |
| | | | 100 | 278 | 244 | 226 | 219 | 100 | 88 | 81 | 79 |
| | | | 500 | 246 | 221 | 203 | 199 | 100 | 90 | 83 | 81 |
| | | Sucrose | 10 | 286 | 227 | 205 | 195 | 100 | 79 | 72 | 68 |
| | | | 25 | 272 | 228 | 203 | 192 | 100 | 84 | 75 | 71 |
| | | | 50 | 286 | 234 | 209 | 195 | 100 | 82 | 73 | 68 |
| | | | 100 | 272 | 230 | 201 | 187 | 100 | 85 | 74 | 69 |
| | | | 250 | 248 | 213 | 189 | 176 | 100 | 86 | 76 | 71 |
| No feces | No addition | No addition | | 268 | 243 | 238 | 239 | 100 | 91 | 89 | 89 |
| | 15 | No addition | | 286 | 262 | 253 | 264 | 100 | 92 | 88 | 92 |
| | | Sorbitol | 10 | 284 | 261 | 249 | 257 | 100 | 92 | 88 | 90 |
| | | | 25 | 287 | 261 | 250 | 265 | 100 | 91 | 87 | 92 |
| | | | 50 | 281 | 261 | 251 | 265 | 100 | 93 | 89 | 94 |
| | | | 100 | 276 | 252 | 244 | 255 | 100 | 91 | 88 | 92 |
| | | | 500 | 242 | 227 | 218 | 230 | 100 | 94 | 90 | 95 |
| | | Sucrose | 10 | 274 | 258 | 251 | 268 | 100 | 94 | 92 | 98 |
| | | | 25 | 277 | 262 | 252 | 268 | 100 | 95 | 91 | 97 |
| | | | 50 | 271 | 253 | 246 | 257 | 100 | 93 | 91 | 95 |
| | | | 100 | 267 | 247 | 241 | 260 | 100 | 93 | 90 | 97 |
| | | | 250 | 238 | 227 | 221 | 235 | 100 | 95 | 93 | 99 |

Example 6

Preservation solutions were prepared through adding 3-carboxyphenylboronic acid (3-CPBA), 3-hydroxyphenylboronic acid (3-HPBA), and 3-aminophenylboronic acid (3-APBA) each at 15 mmol/L as substitute for the phenylboronic acid in the preservation solutions of Example 1 and adding sorbitol, sucrose, or mannitol at 100 mmol/L, and testing was conducted in the same manner as in Example 1. For comparative examples, preservation solutions to which no arylboronic acid was added were prepared, and testing was conducted in the same manner. The results are listed in Table 6. As clearly understood from Table 6, also when other arylboronic acids were used, the recovery ratio of hemoglobin in the sample was further improved in any of fecal specimens of Feces 1, Feces 2, and Feces 3 if sorbitol, sucrose, or mannitol was further added, and it has been recognized that the stability of hemoglobin in the samples containing feces can be synergistically enhanced.

TABLE 6

| | Arylboronic acid (15 mmol/L) | Sugar (100 mmol/L) | Hb concentration (μg/L) Number of days for preservation at 37° C. | | | Recovery ratio with respect to Hb after 0 days (%) Number of days for preservation at 37° C. | | |
|---|---|---|---|---|---|---|---|---|
| | | | 0 days | 7 days | 14 days | 0 days | 7 days | 14 days |
| Feces 1 | No addition | No addition | 315 | 154 | 119 | 100 | 49 | 38 |
| | 3C-PBA | No addition | 309 | 249 | 239 | 100 | 81 | 77 |
| | 3C-PBA | Sorbitol | 305 | 299 | 305 | 100 | 98 | 100 |
| | 3C-PBA | Sucrose | 285 | 260 | 268 | 100 | 91 | 94 |
| | 3C-PBA | Mannitol | 301 | 280 | 306 | 100 | 93 | 102 |
| | 3H-PBA | No addition | 327 | 269 | 268 | 100 | 82 | 82 |
| | 3H-PBA | Sorbitol | 310 | 309 | 303 | 100 | 100 | 98 |
| | 3H-PBA | Sucrose | 311 | 267 | 278 | 100 | 86 | 89 |
| | 3H-PBA | Mannitol | 314 | 302 | 298 | 100 | 96 | 95 |
| | 3A-PBA | No addition | 339 | 275 | 260 | 100 | 81 | 77 |
| | 3A-PBA | Sorbitol | 327 | 316 | 310 | 100 | 97 | 95 |
| Feces 2 | No addition | No addition | 313 | 108 | 78 | 100 | 34 | 25 |
| | 3C-PBA | No addition | 309 | 264 | 240 | 100 | 85 | 78 |
| | 3C-PBA | Sorbitol | 302 | 283 | 260 | 100 | 94 | 86 |
| | 3C-PBA | Sucrose | 286 | 260 | 240 | 100 | 91 | 84 |
| | 3C-PBA | Mannitol | 304 | 290 | 282 | 100 | 95 | 93 |
| | 3H-PBA | No addition | 326 | 277 | 264 | 100 | 85 | 81 |
| | 3H-PBA | Sorbitol | 313 | 304 | 288 | 100 | 97 | 92 |
| | 3H-PBA | Sucrose | 310 | 272 | 262 | 100 | 88 | 84 |
| | 3H-PBA | Mannitol | 315 | 300 | 297 | 100 | 95 | 94 |
| | 3A-PBA | No addition | 330 | 287 | 261 | 100 | 87 | 79 |
| | 3A-PBA | Sorbitol | 315 | 295 | 277 | 100 | 94 | 88 |

TABLE 6-continued

|  | Arylboronic acid (15 mmol/L) | Sugar (100 mmol/L) | Hb concentration (μg/L) Number of days for preservation at 37° C. | | | Recovery ratio with respect to Hb after 0 days (%) Number of days for preservation at 37° C. | | |
|---|---|---|---|---|---|---|---|---|
|  |  |  | 0 days | 7 days | 14 days | 0 days | 7 days | 14 days |
| Feces 3 | No addition | No addition | 304 | 90 | 63 | 100 | 30 | 21 |
|  | 3C-PBA | No addition | 300 | 213 | 200 | 100 | 71 | 67 |
|  | 3C-PBA | Sorbitol | 293 | 251 | 239 | 100 | 85 | 81 |
|  | 3C-PBA | Sucrose | 283 | 226 | 214 | 100 | 80 | 76 |
|  | 3C-PBA | Mannitol | 294 | 241 | 234 | 100 | 82 | 80 |
|  | 3H-PBA | No addition | 313 | 213 | 206 | 100 | 68 | 66 |
|  | 3H-PBA | Sorbitol | 295 | 241 | 229 | 100 | 82 | 78 |
|  | 3H-PBA | Sucrose | 289 | 226 | 210 | 100 | 78 | 73 |
|  | 3H-PBA | Mannitol | 299 | 248 | 241 | 100 | 83 | 81 |
|  | 3A-PBA | No addition | 324 | 227 | 209 | 100 | 70 | 64 |
|  | 3A-PBA | Sorbitol | 313 | 258 | 246 | 100 | 82 | 79 |
| No feces | No addition | No addition | 295 | 276 | 267 | 100 | 94 | 91 |
|  | 3C-PBA | No addition | 293 | 281 | 276 | 100 | 96 | 94 |
|  | 3C-PBA | Sorbitol | 288 | 280 | 271 | 100 | 97 | 94 |
|  | 3C-PBA | Sucrose | 271 | 263 | 257 | 100 | 97 | 95 |
|  | 3C-PBA | Mannitol | 285 | 271 | 267 | 100 | 95 | 94 |
|  | 3H-PBA | No addition | 303 | 294 | 296 | 100 | 97 | 98 |
|  | 3H-PBA | Sorbitol | 300 | 292 | 291 | 100 | 97 | 97 |
|  | 3H-PBA | Sucrose | 283 | 279 | 278 | 100 | 99 | 98 |
|  | 3H-PBA | Mannitol | 296 | 289 | 288 | 100 | 98 | 97 |
|  | 3A-PBA | No addition | 278 | 275 | 272 | 100 | 99 | 98 |
|  | 3A-PBA | Sorbitol | 278 | 275 | 272 | 100 | 99 | 98 |

Example 7

Preservation solutions were prepared through setting the concentration of phenylboronic acid in the preservation solutions of Example 1 to 0 to 50 mmol/L and adding sorbitol or mannitol at 100 mmol/L, and testing was conducted in the same manner as in Example 1. The results are listed in Table 7. As clearly understood from Table 7, in the preservation solutions to which a sugar was added, decrease in the apparent recovery ratios was not observed even when the phenylboronic acid was added at 50 mmol/L. This appears to be because the arylboronic acid has the property of inhibiting the immunoagglutination reaction (at high concentrations), but the existence of a high concentration of the arylboronic acid adversely affects the immunological measurement method to deteriorate the apparent recovery ratio, while on the other hand, when a high concentration of sugar further coexists, the arylboronic acid and the sugar form a complex thereby to suppress the adverse effects of a high concentration of the arylboronic acid on the immunological measurement method.

TABLE 7

|  | Phenyl-boronic acid (mmol/L) | Sugar (100 mmol/L) | Hb concentration (μg/L) Number of days for preservation at 37° C. | | | Recovery ratio with respect to Hb after 0 days (%) Number of days for preservation at 37° C. | | |
|---|---|---|---|---|---|---|---|---|
|  |  |  | 0 days | 7 days | 14 days | 0 days | 7 days | 14 days |
| Feces 1 | No addition | No addition | 315 | 154 | 119 | 100 | 49 | 38 |
|  | 0.5 | Sorbitol | 310 | 206 | 178 | 100 | 66 | 57 |
|  | 15 |  | 301 | 297 | 295 | 100 | 99 | 98 |
|  | 50 |  | 281 | 274 | 275 | 100 | 98 | 98 |
|  | 15 | Mannitol | 301 | 288 | 287 | 100 | 96 | 95 |
|  | 50 |  | 270 | 257 | 255 | 100 | 95 | 95 |
| Feces 2 | No addition | No addition | 313 | 108 | 78 | 100 | 34 | 25 |
|  | 0.5 |  | 301 | 173 | 154 | 100 | 57 | 51 |
|  | 15 | Sorbitol | 299 | 300 | 298 | 100 | 100 | 100 |
|  | 50 |  | 275 | 279 | 284 | 100 | 101 | 103 |
|  | 15 | Mannitol | 298 | 284 | 284 | 100 | 95 | 95 |
|  | 50 |  | 268 | 263 | 274 | 100 | 98 | 102 |
| Feces 3 | No addition | No addition | 304 | 90 | 63 | 100 | 30 | 21 |
|  | 0.5 |  | 294 | 163 | 145 | 100 | 55 | 49 |
|  | 15 | Sorbitol | 292 | 246 | 233 | 100 | 84 | 80 |
|  | 50 |  | 273 | 247 | 230 | 100 | 90 | 84 |
|  | 15 | Mannitol | 288 | 231 | 220 | 100 | 80 | 76 |
|  | 50 |  | 254 | 233 | 226 | 100 | 92 | 89 |
| No feces | No addition | No addition | 295 | 276 | 267 | 100 | 94 | 91 |
|  | 0.5 |  | 291 | 277 | 273 | 100 | 95 | 94 |
|  | 15 | Sorbitol | 288 | 274 | 268 | 100 | 95 | 93 |
|  | 50 |  | 290 | 295 | 293 | 100 | 102 | 101 |
|  | 15 | Mannitol | 287 | 272 | 269 | 100 | 95 | 94 |
|  | 50 |  | 254 | 242 | 241 | 100 | 95 | 95 |

Example 8

Preservation solutions were prepared with the addition of 40 mmol/L HEPES (pH 6.8), 0.1% BSA, 0.1% NaN$_3$, and 0 to 2.5 mmol/L phenylboronic acid. In addition, preservation solutions were also prepared by adding of 0.5 mmol/L 3-carboxyphenylboronic acid (3-CPBA), 3-hydroxyphenylboronic acid (3-HPBA), and 3-aminophenylboronic acid (3-APBA) respectively as substitute for the phenylboronic acid. Samples obtained by adding hemoglobin-added fecal specimens to the preservation solutions so that the fecal concentration would be 0.5% were preserved at 37° C. for 0, 16, 38, and 62 hours. The fecal specimens were added with hemoglobin having an amount such that the hemoglobin concentration in the samples would be about 300 μg/L. Instead of the fecal specimens to which hemoglobin was added, samples containing no fecal specimens, in which hemoglobin was added to the preservation solutions so that the hemoglobin concentration in the samples would be 300 μg/L, were similarly preserved. The hemoglobin (Hb) concentrations (μg/L) in the preserved samples were measured by the latex agglutination method using the same measurement reagent and measurement device as in Example 1.

In the present example, the preservation solutions contain no haptoglobin, so the hemoglobin is decomposed earlier than in Examples 1 to 7, but the stabilizing effect of the arylboronic acid on the hemoglobin was also recognized in the present example. That is, as clearly understood from Table 8, in any of samples of Feces 1, Feces 2, and Feces 3, the recovery ratio of hemoglobin in the sample was improved by adding arylboronic acid at a concentration of 0.25 mmol/L or more. Most of the hemoglobin in the samples is recognized to exist without forming a complex with haptoglobin because no haptoglobin is contained in the preservation solutions unlike Examples 1 to 7. The above results therefore mean that the arylboronic acid also stabilized the hemoglobin which did not form a complex with haptoglobin.

TABLE 8

| | Arylboronic acid (mmol/L) | | Hb concentration (μg/L) Preservation time at 37° C. | | | | Recovery ratio with respect to Hb after 0 days (%) Preservation time at 37° C. | | | |
|---|---|---|---|---|---|---|---|---|---|---|
| | | | 0 h | 16 h | 38 h | 62 h | 0 h | 16 h | 38 h | 62 h |
| Feces 1 | No addition | | 309 | 146 | 39 | 2 | 100 | 47 | 13 | 1 |
| | PBA | 0.25 | 295 | 172 | 74 | 24 | 100 | 58 | 25 | 8 |
| | | 0.5 | 300 | 174 | 74 | 17 | 100 | 58 | 25 | 6 |
| | | 1 | 298 | 182 | 92 | 30 | 100 | 61 | 31 | 10 |
| | | 2.5 | 294 | 177 | 80 | 23 | 100 | 60 | 27 | 8 |
| | 3-CPBA | 0.5 | 296 | 163 | 68 | 20 | 100 | 55 | 23 | 7 |
| | 3-HPBA | 0.5 | 298 | 171 | 79 | 25 | 100 | 57 | 26 | 8 |
| | 3-APBA | 0.5 | 318 | 178 | 92 | 31 | 100 | 56 | 29 | 10 |
| Feces 2 | No addition | | 282 | 54 | 0 | 0 | 100 | 19 | 0 | 0 |
| | PBA | 0.25 | 298 | 103 | 10 | 0 | 100 | 35 | 3 | 0 |
| | | 0.5 | 299 | 103 | 10 | 0 | 100 | 34 | 3 | 0 |
| | | 1 | 299 | 119 | 17 | 0 | 100 | 40 | 6 | 0 |
| | | 2.5 | 299 | 124 | 18 | 0 | 100 | 41 | 6 | 0 |
| | 3-CPBA | 0.5 | 288 | 90 | 8 | 0 | 100 | 31 | 3 | 0 |
| | 3-HPBA | 0.5 | 295 | 95 | 11 | 0 | 100 | 32 | 4 | 0 |
| | 3-APBA | 0.5 | 303 | 89 | 4 | 0 | 100 | 29 | 1 | 0 |
| Feces 3 | No addition | | 277 | 36 | 0 | 0 | 100 | 13 | 0 | 0 |
| | PBA | 0.25 | 284 | 92 | 8 | 0 | 100 | 32 | 3 | 0 |
| | | 0.5 | 289 | 92 | 8 | 0 | 100 | 32 | 3 | 0 |
| | | 1 | 287 | 112 | 14 | 0 | 100 | 39 | 5 | 0 |
| | | 2.5 | 293 | 119 | 18 | 0 | 100 | 41 | 6 | 0 |
| | 3-CPBA | 0.5 | 281 | 95 | 5 | 0 | 100 | 34 | 2 | 0 |
| | 3-HPBA | 0.5 | 295 | 106 | 9 | 0 | 100 | 36 | 3 | 0 |
| | 3-APBA | 0.5 | 298 | 94 | 4 | 0 | 100 | 31 | 1 | 0 |
| No feces | No addition | | 303 | 274 | 252 | 240 | 100 | 91 | 83 | 79 |
| | PBA | 0.25 | 303 | 281 | 263 | 265 | 100 | 93 | 87 | 88 |
| | | 0.5 | 295 | 284 | 270 | 263 | 100 | 96 | 91 | 89 |
| | | 1 | 292 | 276 | 261 | 259 | 100 | 95 | 90 | 89 |
| | | 2.5 | 291 | 273 | 257 | 259 | 100 | 94 | 88 | 89 |
| | 3-CPBA | 0.5 | 299 | 279 | 264 | 266 | 100 | 94 | 88 | 89 |
| | 3-HPBA | 0.5 | 306 | 282 | 263 | 264 | 100 | 92 | 86 | 86 |
| | 3-APBA | 0.5 | 312 | 291 | 274 | 274 | 100 | 93 | 88 | 88 |

Example 9

The concentration of phenylboronic acid in the preservation solutions of Example 8 was fixed to 0.5 mmol/L, preservation solutions to which sorbitol or sucrose was further added at 10 to 250 mmol/L or trehalose, glucose, fructose, or mannitol was further added at 50 to 100 mmol/L were prepared, and testing was conducted in the same manner as in Example 8. In addition, preservation solutions to which the phenylboronic acid was added but no sugar was added were prepared, preservation solutions to which the phenylboronic acid and sugar were not added were prepared for the comparative examples, and testing was conducted in the same manner. The results are listed in Tables 9A and 9B. As clearly understood from Tables 9A and 9B, even in the preservation solutions containing no haptoglobin, when the phenylboronic acid was further added with sorbitol, sucrose, trehalose, glucose, fructose, or mannitol, the recovery ratio of hemoglobin in the sample was further improved in any of fecal specimens of Feces 1, Feces 2, and Feces 3. Moreover, even when a sugar is added to the preservation solutions containing no phenylboronic acid, the recovery ratio of hemoglobin in the samples containing fecal specimens is not improved. These results indicate that even with the preservation solutions containing no haptoglobin, a synergistic effect between the phenylboronic acid and various sugars can be obtained as in Examples 2 to 7.

TABLE 9A

| | Phenyl-boronic acid (mmol/L) | Sugar (mmol/L) | | Hb concentration (µg/L) Preservation time at 37° C. | | | | Recovery ratio with respect to Hb after 0 days (%) Preservation time at 37° C. | | | |
|---|---|---|---|---|---|---|---|---|---|---|---|
| | | | | 0 h | 16 h | 38 h | 62 h | 0 h | 16 h | 38 h | 62 h |
| Feces 1 | No addition | No addition | | 309 | 146 | 39 | 2 | 100 | 47 | 13 | 1 |
| | 0.5 | No addition | | 300 | 174 | 74 | 17 | 100 | 58 | 25 | 6 |
| | 0.5 | Sorbitol | 10 | 300 | 179 | 81 | 20 | 100 | 60 | 27 | 7 |
| | 0.5 | | 50 | 290 | 175 | 81 | 21 | 100 | 61 | 28 | 7 |
| | 0.5 | | 100 | 289 | 177 | 90 | 28 | 100 | 61 | 31 | 10 |
| | 0.5 | | 250 | 277 | 182 | 105 | 45 | 100 | 65 | 38 | 16 |
| | No addition | | 100 | 290 | 146 | 39 | 1 | 100 | 50 | 13 | 0 |
| | 0.5 | Sucrose | 10 | 294 | 169 | 79 | 28 | 100 | 57 | 27 | 9 |
| | 0.5 | | 50 | 284 | 173 | 92 | 34 | 100 | 61 | 33 | 12 |
| | 0.5 | | 100 | 273 | 166 | 88 | 31 | 100 | 61 | 32 | 11 |
| | 0.5 | | 250 | 249 | 167 | 97 | 43 | 100 | 67 | 39 | 17 |
| | No addition | | 100 | 271 | 137 | 45 | 10 | 100 | 51 | 16 | 4 |
| | 0.5 | Trehalose | 50 | 285 | 168 | 81 | 26 | 100 | 59 | 28 | 9 |
| | 0.5 | | 100 | 272 | 164 | 78 | 27 | 100 | 61 | 29 | 10 |
| | No addition | | 100 | 268 | 133 | 41 | 8 | 100 | 50 | 15 | 3 |
| | 0.5 | Glucose | 50 | 282 | 176 | 84 | 27 | 100 | 63 | 30 | 10 |
| | 0.5 | | 100 | 278 | 178 | 92 | 32 | 100 | 64 | 33 | 12 |
| | No addition | | 100 | 281 | 136 | 32 | 0 | 100 | 49 | 12 | 0 |
| | 0.5 | Fructose | 50 | 286 | 182 | 102 | 41 | 100 | 64 | 36 | 14 |
| | 0.5 | | 100 | 290 | 185 | 105 | 46 | 100 | 64 | 36 | 16 |
| | No addition | | 100 | 281 | 134 | 35 | 0 | 100 | 48 | 12 | 0 |
| | 0.5 | Mannitol | 50 | 279 | 176 | 90 | 34 | 100 | 63 | 32 | 12 |
| | 0.5 | | 100 | 277 | 173 | 91 | 32 | 100 | 62 | 33 | 12 |
| | No addition | | 100 | 276 | 131 | 29 | 1 | 100 | 48 | 10 | 0 |
| Feces 2 | No addition | No addition | | 282 | 54 | 0 | 0 | 100 | 19 | 0 | 0 |
| | 0.5 | No addition | | 299 | 103 | 10 | 0 | 100 | 34 | 3 | 0 |
| | 0.5 | Sorbitol | 10 | 299 | 102 | 8 | 0 | 100 | 34 | 3 | 0 |
| | 0.5 | | 50 | 292 | 107 | 10 | 0 | 100 | 37 | 4 | 0 |
| | 0.5 | | 100 | 288 | 110 | 15 | 0 | 100 | 38 | 5 | 0 |
| | 0.5 | | 250 | 275 | 117 | 20 | 0 | 100 | 43 | 7 | 0 |
| | No addition | | 100 | 275 | 61 | 0 | 0 | 100 | 22 | 0 | 0 |
| | 0.5 | Sucrose | 10 | 297 | 100 | 15 | 0 | 100 | 34 | 5 | 0 |
| | 0.5 | | 50 | 282 | 106 | 17 | 0 | 100 | 38 | 6 | 0 |
| | 0.5 | | 100 | 276 | 107 | 19 | 0 | 100 | 39 | 7 | 0 |
| | 0.5 | | 250 | 249 | 107 | 23 | 0 | 100 | 43 | 9 | 0 |
| | No addition | | 100 | 255 | 57 | 3 | 0 | 100 | 22 | 1 | 0 |
| | 0.5 | Trehalose | 50 | 278 | 97 | 14 | 0 | 100 | 35 | 5 | 0 |
| | 0.5 | | 100 | 267 | 102 | 15 | 0 | 100 | 38 | 6 | 0 |
| | No addition | | 100 | 254 | 54 | 1 | 0 | 100 | 21 | 0 | 0 |
| | 0.5 | Glucose | 50 | 281 | 102 | 10 | 0 | 100 | 36 | 4 | 0 |
| | 0.5 | | 100 | 278 | 105 | 8 | 0 | 100 | 38 | 3 | 0 |
| | No addition | | 100 | 256 | 54 | 0 | 0 | 100 | 21 | 0 | 0 |
| | 0.5 | Fructose | 50 | 290 | 114 | 20 | 0 | 100 | 39 | 7 | 0 |
| | 0.5 | | 100 | 283 | 116 | 21 | 0 | 100 | 41 | 7 | 0 |
| | No addition | | 100 | 268 | 60 | 1 | 0 | 100 | 22 | 0 | 0 |
| | 0.5 | Mannitol | 50 | 287 | 115 | 21 | 0 | 100 | 40 | 7 | 0 |
| | 0.5 | | 100 | 284 | 116 | 23 | 0 | 100 | 41 | 8 | 0 |
| | No addition | | 100 | 266 | 55 | 1 | 0 | 100 | 21 | 0 | 0 |

TABLE 9B

| | Phenyl-boronic acid (mmol/L) | Sugar (mmol/L) | | Hb concentration (µg/L) Preservation time at 37° C. | | | | Recovery ratio with respect to Hb after 0 days (%) Preservation time at 37° C. | | | |
|---|---|---|---|---|---|---|---|---|---|---|---|
| | | | | 0 h | 16 h | 38 h | 62 h | 0 h | 16 h | 38 h | 62 h |
| Feces 3 | No addition | No addition | | 277 | 36 | 0 | 0 | 100 | 13 | 0 | 0 |
| | 0.5 | No addition | | 289 | 92 | 8 | 0 | 100 | 32 | 3 | 0 |
| | 0.5 | Sorbitol | 10 | 294 | 105 | 12 | 0 | 100 | 36 | 4 | 0 |
| | 0.5 | | 50 | 296 | 111 | 15 | 0 | 100 | 38 | 5 | 0 |
| | 0.5 | | 100 | 285 | 124 | 19 | 1 | 100 | 43 | 7 | 0 |
| | 0.5 | | 250 | 274 | 134 | 25 | 2 | 100 | 49 | 9 | 1 |
| | No addition | | 100 | 277 | 49 | 1 | 0 | 100 | 18 | 0 | 0 |
| | 0.5 | Sucrose | 10 | 294 | 114 | 13 | 0 | 100 | 39 | 4 | 0 |
| | 0.5 | | 50 | 286 | 110 | 11 | 0 | 100 | 38 | 4 | 0 |
| | 0.5 | | 100 | 268 | 102 | 9 | 0 | 100 | 38 | 3 | 0 |
| | 0.5 | | 250 | 244 | 114 | 17 | 0 | 100 | 47 | 7 | 0 |
| | No addition | | 100 | 257 | 67 | 0 | 0 | 100 | 26 | 0 | 0 |
| | 0.5 | Trehalose | 50 | 279 | 96 | 8 | 0 | 100 | 34 | 3 | 0 |
| | 0.5 | | 100 | 264 | 91 | 7 | 0 | 100 | 35 | 3 | 0 |

TABLE 9B-continued

| | Phenyl-boronic acid (mmol/L) | Sugar (mmol/L) | | Hb concentration (µg/L) Preservation time at 37° C. | | | | Recovery ratio with respect to Hb after 0 days (%) Preservation time at 37° C. | | | |
|---|---|---|---|---|---|---|---|---|---|---|---|
| | | | | 0 h | 16 h | 38 h | 62 h | 0 h | 16 h | 38 h | 62 h |
| | No addition | Glucose | 100 | 260 | 48 | 0 | 0 | 100 | 19 | 0 | 0 |
| | 0.5 | Glucose | 50 | 285 | 112 | 15 | 0 | 100 | 39 | 5 | 0 |
| | 0.5 | | 100 | 276 | 110 | 16 | 0 | 100 | 40 | 6 | 0 |
| | No addition | | 100 | 270 | 46 | 1 | 0 | 100 | 17 | 0 | 0 |
| | 0.5 | Fructose | 50 | 286 | 119 | 16 | 0 | 100 | 42 | 6 | 0 |
| | 0.5 | | 100 | 288 | 130 | 22 | 0 | 100 | 45 | 8 | 0 |
| | No addition | | 100 | 263 | 51 | 0 | 0 | 100 | 19 | 0 | 0 |
| | 0.5 | | 100 | 288 | 96 | 6 | 0 | 100 | 33 | 2 | 0 |
| | No addition | | 100 | 269 | 57 | 0 | 0 | 100 | 21 | 0 | 0 |
| No feces | No addition | No addition | | 303 | 274 | 252 | 240 | 100 | 91 | 83 | 79 |
| | 0.5 | No addition | | 295 | 284 | 270 | 263 | 100 | 96 | 91 | 89 |
| | 0.5 | Sorbitol | 10 | 296 | 277 | 263 | 259 | 100 | 94 | 89 | 87 |
| | 0.5 | | 50 | 290 | 273 | 250 | 252 | 100 | 94 | 86 | 87 |
| | 0.5 | | 100 | 289 | 266 | 247 | 255 | 100 | 92 | 86 | 88 |
| | 0.5 | | 250 | 276 | 262 | 245 | 245 | 100 | 95 | 89 | 89 |
| | No addition | | 100 | 300 | 263 | 245 | 235 | 100 | 88 | 82 | 79 |
| | 0.5 | Sucrose | 10 | 304 | 271 | 255 | 258 | 100 | 89 | 84 | 85 |
| | 0.5 | | 50 | 293 | 272 | 251 | 251 | 100 | 93 | 86 | 86 |
| | 0.5 | | 100 | 278 | 260 | 244 | 249 | 100 | 93 | 88 | 89 |
| | 0.5 | | 250 | 258 | 241 | 228 | 226 | 100 | 93 | 88 | 88 |
| | No addition | | 100 | 278 | 245 | 229 | 224 | 100 | 88 | 83 | 81 |
| | 0.5 | Trehalose | 50 | 284 | 260 | 249 | 253 | 100 | 91 | 88 | 89 |
| | 0.5 | | 100 | 276 | 254 | 246 | 242 | 100 | 92 | 89 | 88 |
| | No addition | | 100 | 280 | 241 | 228 | 219 | 100 | 86 | 81 | 78 |
| | 0.5 | Glucose | 50 | 292 | 272 | 260 | 257 | 100 | 93 | 89 | 88 |
| | 0.5 | | 100 | 287 | 267 | 255 | 254 | 100 | 93 | 89 | 89 |
| | No addition | | 100 | 283 | 256 | 230 | 218 | 100 | 90 | 81 | 77 |
| | 0.5 | Fructose | 50 | 296 | 271 | 254 | 256 | 100 | 91 | 86 | 86 |
| | 0.5 | | 100 | 292 | 265 | 254 | 262 | 100 | 91 | 87 | 90 |
| | No addition | | 100 | 284 | 246 | 233 | 230 | 100 | 86 | 82 | 81 |
| | 0.5 | Mannitol | 50 | 292 | 273 | 255 | 259 | 100 | 94 | 87 | 89 |
| | 0.5 | | 100 | 285 | 266 | 250 | 259 | 100 | 93 | 87 | 91 |
| | No addition | | 100 | 281 | 254 | 237 | 235 | 100 | 91 | 84 | 84 |

Preservation solutions were prepared through fixing the concentration of phenylboronic acid in the preservation solutions of Example 8 to 0.5 mmol/L, adding of 0.5 mmol/L 3-carboxyphenylboronic acid (3-CPBA), 3-hydroxyphenylboronic acid (3-HPBA), and 3-aminophenylboronic acid (3-APBA) respectively as substitute for the phenylboronic acid, and adding sorbitol or sucrose at 100 mmol/L, and testing was conducted in the same manner as in Example 8. For comparative examples, preservation solutions to which no arylboronic acid was added were prepared, and testing was conducted in the same manner. The results are listed in Table 10. As clearly understood from Table 10, even with the preservation solutions containing no haptoglobin, the combined use of various arylboronic acids and sugars further improve the recovery ratio of hemoglobin in the samples, and it has been recognized that the stability of hemoglobin in the samples containing feces can be synergistically enhanced.

TABLE 10

| | Arylboronic acid (0.5 mmol/L) | Sugar (100 mmol/L) | Hb concentration (µg/L) Preservation time at 37° C. | | | | Recovery ratio with respect to Hb after 0 days (%) Preservation time at 37° C. | | | |
|---|---|---|---|---|---|---|---|---|---|---|
| | | | 0 h | 16 h | 38 h | 62 h | 0 h | 16 h | 38 h | 62 h |
| Feces 1 | No addition | No addition | 309 | 146 | 39 | 2 | 100 | 47 | 13 | 1 |
| | PBA | No addition | 300 | 174 | 74 | 17 | 100 | 58 | 25 | 6 |
| | | Sorbitol | 289 | 177 | 90 | 28 | 100 | 61 | 31 | 10 |
| | | Sucrose | 273 | 166 | 88 | 31 | 100 | 61 | 32 | 11 |
| | 3-CPBA | No addition | 296 | 163 | 68 | 20 | 100 | 55 | 23 | 7 |
| | | Sorbitol | 290 | 173 | 89 | 31 | 100 | 59 | 30 | 11 |
| | | Sucrose | 274 | 160 | 64 | 15 | 100 | 58 | 23 | 6 |
| | 3-HPBA | No addition | 298 | 171 | 79 | 25 | 100 | 57 | 26 | 8 |
| | | Sorbitol | 295 | 195 | 118 | 56 | 100 | 66 | 40 | 19 |
| | | Sucrose | 278 | 170 | 86 | 28 | 100 | 61 | 31 | 10 |
| | 3-APBA | No addition | 318 | 178 | 92 | 31 | 100 | 56 | 29 | 10 |
| | | Sorbitol | 293 | 177 | 97 | 36 | 100 | 60 | 33 | 12 |
| | | Sucrose | 277 | 168 | 75 | 21 | 100 | 61 | 27 | 8 |
| Feces 2 | No addition | No addition | 282 | 54 | 0 | 0 | 100 | 19 | 0 | 0 |
| | PBA | No addition | 299 | 103 | 10 | 0 | 100 | 34 | 3 | 0 |
| | | Sorbitol | 288 | 110 | 15 | 0 | 100 | 38 | 5 | 0 |
| | | Sucrose | 276 | 107 | 19 | 0 | 100 | 39 | 7 | 0 |

TABLE 10-continued

| | Arylboronic acid (0.5 mmol/L) | Sugar (100 mmol/L) | Hb concentration (μg/L) Preservation time at 37° C. | | | | Recovery ratio with respect to Hb after 0 days (%) Preservation time at 37° C. | | | |
|---|---|---|---|---|---|---|---|---|---|---|
| | | | 0 h | 16 h | 38 h | 62 h | 0 h | 16 h | 38 h | 62 h |
| | 3-CPBA | No addition | 288 | 90 | 8 | 0 | 100 | 31 | 3 | 0 |
| | | Sorbitol | 283 | 99 | 13 | 0 | 100 | 35 | 4 | 0 |
| | | Sucrose | 265 | 86 | 6 | 0 | 100 | 32 | 2 | 0 |
| | 3-HPBA | No addition | 295 | 95 | 11 | 0 | 100 | 32 | 4 | 0 |
| | | Sorbitol | 288 | 100 | 14 | 0 | 100 | 35 | 5 | 0 |
| | | Sucrose | 262 | 95 | 9 | 0 | 100 | 36 | 3 | 0 |
| | 3-APBA | No addition | 303 | 89 | 4 | 0 | 100 | 29 | 1 | 0 |
| | | Sorbitol | 286 | 103 | 14 | 0 | 100 | 36 | 5 | 0 |
| | | Sucrose | 270 | 91 | 9 | 0 | 100 | 34 | 3 | 0 |
| Feces 3 | No addition | No addition | 277 | 36 | 0 | 0 | 100 | 13 | 0 | 0 |
| | PBA | No addition | 289 | 92 | 8 | 0 | 100 | 32 | 3 | 0 |
| | | Sorbitol | 285 | 124 | 19 | 1 | 100 | 43 | 7 | 0 |
| | | Sucrose | 268 | 102 | 9 | 0 | 100 | 38 | 3 | 0 |
| | 3-CPBA | No addition | 281 | 95 | 5 | 0 | 100 | 34 | 2 | 0 |
| | | Sorbitol | 283 | 117 | 15 | 0 | 100 | 41 | 5 | 0 |
| | | Sucrose | 267 | 92 | 9 | 0 | 100 | 34 | 4 | 0 |
| | 3-HPBA | No addition | 295 | 106 | 9 | 0 | 100 | 36 | 3 | 0 |
| | | Sorbitol | 287 | 113 | 12 | 0 | 100 | 39 | 4 | 0 |
| | | Sucrose | 266 | 94 | 8 | 0 | 100 | 35 | 3 | 0 |
| | 3-APBA | No addition | 298 | 94 | 4 | 0 | 100 | 31 | 1 | 0 |
| | | Sorbitol | 284 | 116 | 10 | 0 | 100 | 41 | 4 | 0 |
| | | Sucrose | 273 | 99 | 13 | 0 | 100 | 36 | 5 | 0 |
| No feces | No addition | No addition | 303 | 274 | 252 | 240 | 100 | 91 | 83 | 79 |
| | PBA | No addition | 295 | 284 | 270 | 263 | 100 | 96 | 91 | 89 |
| | | Sorbitol | 289 | 266 | 247 | 255 | 100 | 92 | 86 | 88 |
| | | Sucrose | 278 | 260 | 244 | 249 | 100 | 93 | 88 | 89 |
| | 3-CPBA | No addition | 299 | 279 | 264 | 266 | 100 | 94 | 88 | 89 |
| | | Sorbitol | 287 | 271 | 253 | 254 | 100 | 94 | 88 | 89 |
| | | Sucrose | 281 | 254 | 246 | 247 | 100 | 91 | 88 | 88 |
| | 3-HPBA | No addition | 306 | 282 | 263 | 264 | 100 | 92 | 86 | 86 |
| | | Sorbitol | 294 | 273 | 259 | 259 | 100 | 93 | 88 | 88 |
| | | Sucrose | 276 | 261 | 248 | 248 | 100 | 95 | 90 | 90 |
| | 3-APBA | No addition | 312 | 291 | 274 | 274 | 100 | 93 | 88 | 88 |
| | | Sorbitol | 300 | 279 | 265 | 268 | 100 | 93 | 88 | 89 |
| | | Sucrose | 293 | 227 | 261 | 257 | 100 | 94 | 89 | 88 |

The invention claimed is:

1. A method of stabilizing a protein contained in a specimen derived from a living body, the method comprising a step of causing the protein contained in the specimen derived from the living body to coexist with an arylboronic acid and a sugar in a solution, wherein
the protein contained in the specimen derived from the living body is at least one selected from the group consisting of hemoglobin, haptoglobin, and a hemoglobin-haptoglobin complex.

2. The method according to claim 1, wherein the arylboronic acid is at least one selected from the group consisting of phenylboronic acid and derivatives thereof.

3. The method according to claim 1, wherein the arylboronic acid is at least one selected from the group consisting of phenylboronic acid, hydroxyphenylboronic acid, carboxyphenylboronic acid, aminophenylboronic acid, and salts thereof.

4. The method according to claim 1, wherein
the causing the protein contained in the specimen derived from the living body to coexist with an arylboronic acid comprises dispersing the protein contained in the specimen derived from the living body in a solution containing the arylboronic acid, and
a concentration of the arylboronic acid in the solution is 0.1 mmol/L or more.

5. The method according to claim 1, wherein the sugar is at least one selected from the group consisting of sugar alcohol, monosaccharide, and disaccharide.

6. The method according to claim 1, wherein the sugar is at least one selected from the group consisting of sorbitol, glucose, mannitol, fructose, xylitol, erythritol, sucrose, trehalose, lactose, and maltose.

7. The method according to claim 1, wherein
the causing the protein contained in the specimen derived from the living body to coexist with the arylboronic acid and a sugar comprises dispersing the protein contained in the specimen derived from the living body in the solution containing the arylboronic acid and the sugar, and
a concentration of the sugar in the solution is 5 mmol/L or more.

8. The method according to claim 1, wherein
the specimen derived from the living body contains at least hemoglobin, and
the method further comprises bringing the hemoglobin and haptoglobin into contact with each other to form a complex of hemoglobin and haptoglobin.

9. The method according to claim 1, wherein the specimen derived from the living body is feces, saliva, or urine.

10. A stabilizing solution for stabilizing a protein contained in a specimen derived from a living body, wherein
the stabilizing solution comprises an arylboronic acid, a sugar, and
the protein contained in the specimen derived from the living body is at least one selected from the group consisting of hemoglobin, haptoglobin, and a hemoglobin-haptoglobin complex.

11. The stabilizing solution according to claim 10, wherein the arylboronic acid is at least one selected from the group consisting of phenylboronic acid and derivatives thereof.

12. The stabilizing solution according to claim 10, wherein the arylboronic acid is at least one selected from the group consisting of phenylboronic acid, hydroxyphenylboronic acid, carboxyphenylboronic acid, aminophenylboronic acid, and salts thereof.

13. The stabilizing solution according to claim 10, wherein the sugar is at least one selected from the group consisting of sorbitol, glucose, mannitol, fructose, xylitol, erythritol, sucrose, trehalose, lactose, and maltose.

14. The stabilizing solution according to claim 10, comprising haptoglobin.

15. The stabilizing solution according to claim 10, wherein the specimen is feces, saliva, or urine.

16. The stabilizing solution according to claim 10, wherein the stabilizing solution is a solution for preserving the specimen derived from the living body.

17. A method of detecting a protein in a specimen derived from a living body, the method comprising:
adding the specimen derived from the living body to the stabilizing solution according to claim 11 to obtain a sample containing the specimen; and
detecting the protein in the sample by an immunological measurement method, wherein
the protein in the specimen derived from the living body is at least one selected from the group consisting of hemoglobin, haptoglobin, and a hemoglobin-haptoglobin complex.

18. The method according to claim 17, wherein
the specimen derived from the living body contains at least hemoglobin, and
the hemoglobin in the sample forms a complex together with haptoglobin.

19. The method according to claim 18, wherein the stabilizing solution further comprises haptoglobin.

* * * * *